US 6,713,019 B2

(12) United States Patent
Ozasa et al.

(10) Patent No.: US 6,713,019 B2
(45) Date of Patent: Mar. 30, 2004

(54) FLOW CYTOMETER

(75) Inventors: Masatsugu Ozasa, Kasai (JP); Tatsuya Kosako, Kakogawa (JP)

(73) Assignee: Sysmex Corporation, Hyogo (JP)

( * ) Notice: Subject to any disclaimer, the term of this patent is extended or adjusted under 35 U.S.C. 154(b) by 56 days.

(21) Appl. No.: 10/106,062

(22) Filed: Mar. 27, 2002

(65) Prior Publication Data

US 2002/0141902 A1 Oct. 3, 2002

(30) Foreign Application Priority Data

Mar. 29, 2001 (JP) ........................................ 2001-094878
Jun. 15, 2001 (JP) ........................................ 2001-182085

(51) Int. Cl.$^7$ .............................................. G01N 21/17
(52) U.S. Cl. ................................ 422/82.09; 422/82.05; 436/63; 436/164; 356/317; 356/318; 356/337; 356/338
(58) Field of Search .............................. 436/10, 63, 52, 436/164, 165, 172; 422/73, 81, 82.05, 82.08, 82.09; 356/317, 318, 336, 337, 338

(56) References Cited

U.S. PATENT DOCUMENTS

| 4,636,075 A | 1/1987 | Knollenberg |
| 4,920,275 A | 4/1990 | Itoh |
| 5,480,775 A | * 1/1996 | Ito et al. ........................ 435/7.2 |
| 5,677,183 A | * 10/1997 | Takarada et al. ............... 436/10 |
| 5,693,484 A | * 12/1997 | Nakamoto et al. ............ 435/39 |
| 5,757,476 A | * 5/1998 | Nakamoto et al. ............ 356/73 |

FOREIGN PATENT DOCUMENTS

| EP | 0 564 122 A | 10/1993 |
| EP | 0 696 731 A | 2/1996 |
| JP | 63-253237 | * 10/1988 |

* cited by examiner

Primary Examiner—Maureen M. Wallenhorst
(74) Attorney, Agent, or Firm—Birch, Stewart, Kolasch & Birch, LLP

(57) ABSTRACT

A flow cytometer includes a flow cell for flowing a sample liquid in a flowing direction, to form a sample flow the sample liquid containing particles to be analyzed, a laser diode radiating a laser beam having an elliptic cross section, a beam collimating section for collimating the laser beam radiated from the laser diode, a beam spot forming section for focusing the collimated beam at the sample flow in the flow cell to form a beam spot, and a light receiving section for receiving light generated from the particles at the beam spot to detect optical information of the particles, wherein the laser diode is arranged such that a minor diameter of the elliptic section of the laser beam is parallel to the sample flow.

17 Claims, 10 Drawing Sheets

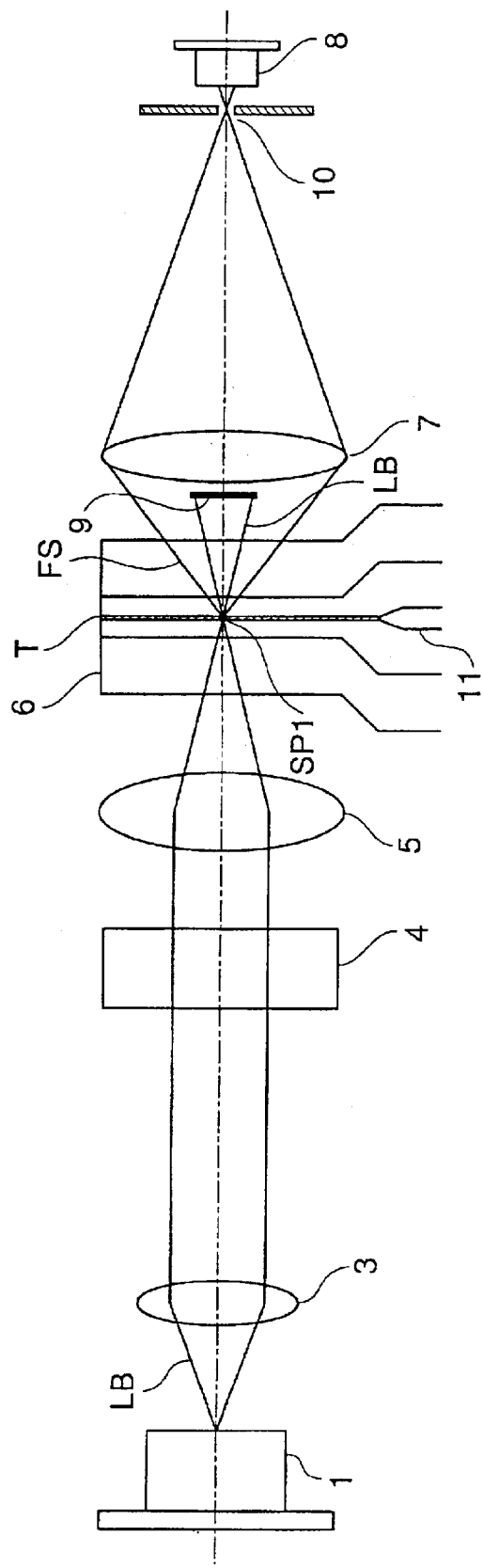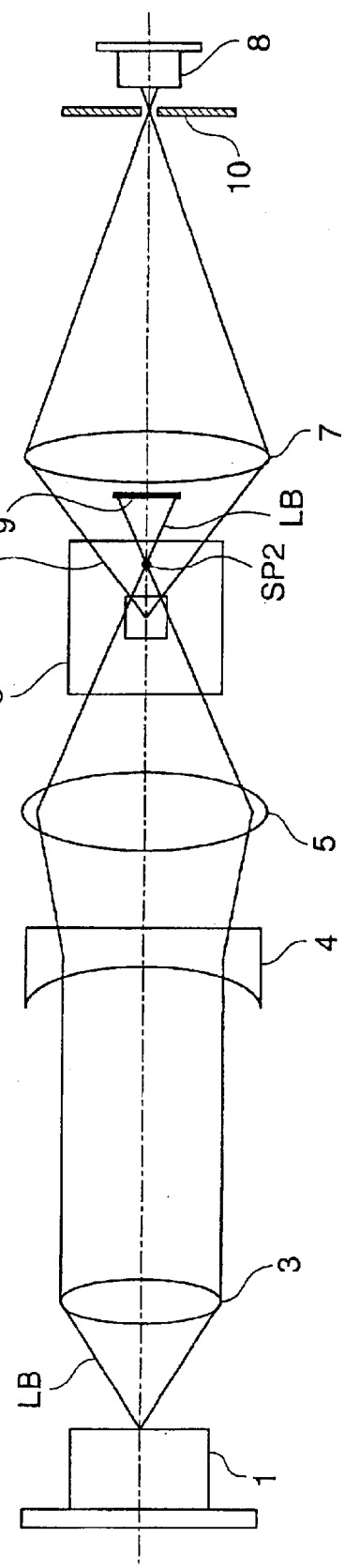

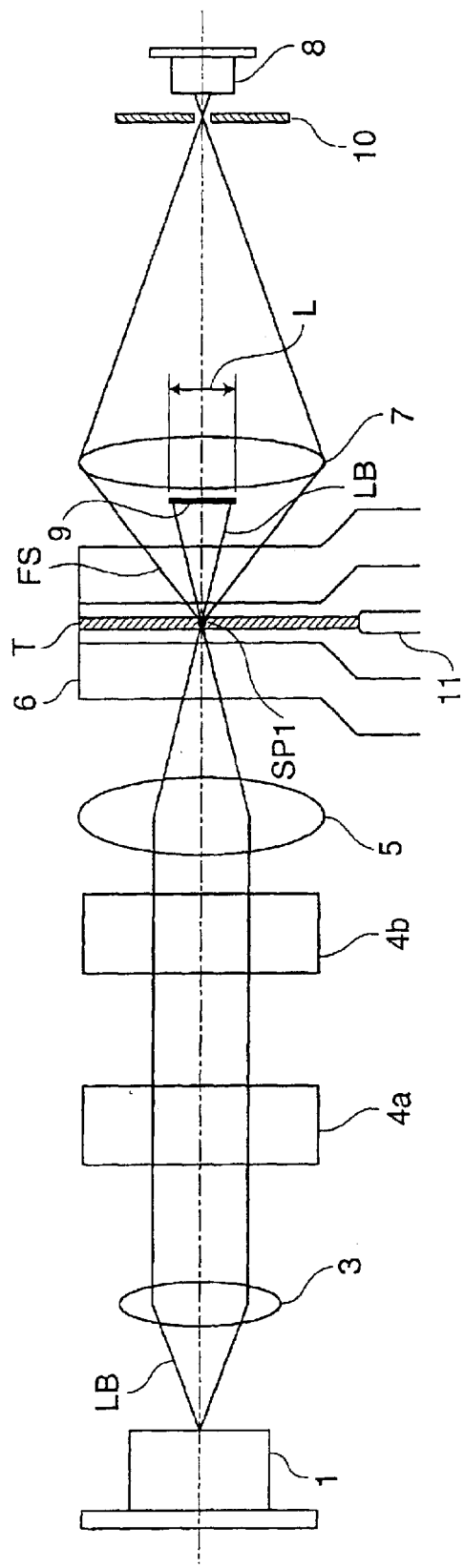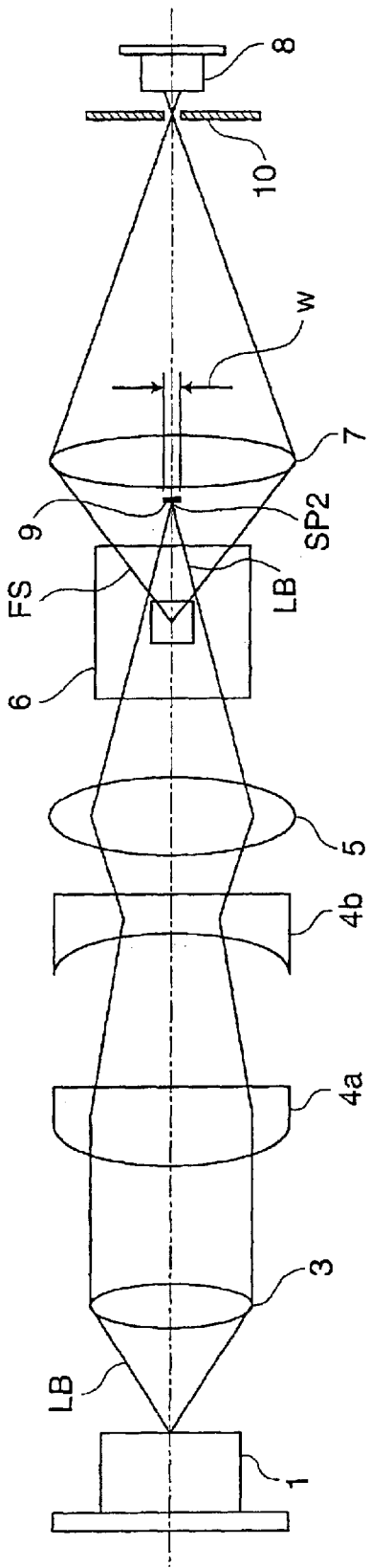

FLOW CYTOMETER

CROSS-REFERENCE TO RELATED APPLICATION

This application is related to Japanese Patent Applications Nos. 2001-094878 filed in Mar. 29, 2001 and 2001-182085 filed in Jun. 15, 2001, whose priorities are claimed under 35 USC §119, the disclosures of which are incorporated by reference in their entirety.

BACKGROUND OF THE INVENTION

1. Field of the Invention

The present invention relates to a flow cytometer for optically detecting and analyzing particles such as blood cells in blood, material components contained in urine or the like.

2. Description of the Related Art

Various particle analyzers have been developed for automatically detecting and analyzing particles contained in a specimen, for example, blood cells in blood such as red blood cells, white blood cells and blood platelets, or material components in urine such as bacteria, blood cells, white blood cells, epithelial cells or casts. A flow cytometer is well known as such a particle analyzer. The flow cytometer includes a detecting section with a flow cell, a laser and a photoelectric conversion element. The flow cell surrounds a sample liquid containing particles to be analyzed with a sheath fluid to converge the sample liquid into a thin flow so that the particles align and pass therethrough. The laser irradiates the passing particles with a laser beam to obtain light generated from each particle i.e., optical information. The optical information includes scattered light such as forward scattered light, sideward scattered light, backward scattered light, fluorescence or the like. The optical information is suitably selected depending upon an analyzed target. The photoelectric conversion element detects the optical information to generate a pulsed electrical signal.

A waveform of the electrical signal obtained as mentioned above is processed to calculate a parameter representing the characteristics of each particle and the particles to be analyzed are classified and counted based on the parameter.

In the optical information, an intensity of the light is recognized as a height (peak level) of the signal waveform, and at the same time, a light emitting period (pulse width) is clocked. That is, the above parameter includes the peak level and the pulse width. For example, the peak level of the signal of the forward scattered light (hereinafter referred to as a "particle signal") represents a size of a particle, while the pulse width represents a length of a particle. In case where a fluorescent staining is performed in advance to particles, for example, nucleated cells, a fluorescent signal can be obtained from each particle. The peak level of the signal represents a staining degree of the nuclear or the like, while the pulse width represents a length of the fluorescent staining portion. A histogram, formed based upon the parameter representing the characteristics of each particle or a scattergram showing a distribution of the particles, is formed by combining a plurality of parameters, whereby the type or number of the particles contained in the sample is statistically analyzed.

In recent years, the above-mentioned flow cytometer generally utilizes a laser diode from which the laser beam is irradiated to the flow cell.

FIG. 1 is a schematic view showing one example of an optical system in a conventional flow cytometer using a laser diode 1 for a light source. A sample liquid T containing particles to be analyzed is supplied from a nozzle 11 into the flow cell 6 in the direction shown by an arrow A. A sheath liquid S is supplied to the flow cell 6 for surrounding the supplied sample liquid T, whereby the sample liquid T is converged into a thin sample flow by a hydrodynamic effect. As a result, the sample flow is passed through the flow cell 6 with the particles aligned. A radiant laser beam LB emitted from the laser diode 1 is collimated by a collimator lens 3, and then, passes through a cylindrical lens 4 and a condenser lens 5 to form a beam spot at a position R of the flow of the sample liquid T in the flow cell 6.

As shown in FIG. 2, the laser diode 1 has inherent features that the laser beam LB is diffusible and has an elliptic cross section. Thus, the laser beam LB emitted from the laser diode 1 along an optical axis in the direction of Z has radiation angles defined by a large angle $\theta1$ in the direction of a major diameter of the ellipse, i.e., in the direction of X, and a small angle $\theta2$ in the direction of a minor diameter of the ellipse, i.e., in the direction of Y.

In FIG. 1, increasing the radiation angle $\theta$ of the laser beam with respect to the flowing direction of the sample liquid T, that is, increasing a collimated beam width d in the same direction brings the following merits:

1. The amount of light of the beam spot at the position R can be increased.
2. The diameter of the beam spot in the flowing direction of the sample liquid T can be decreased in view of a diffraction limit of the beam, since the laser beam is such a Gaussian beam that the Gaussian beam of a larger diameter is less divergent than that of a smaller diameter.

These merits bring the effects of enhancing detecting sensitivity and preventing simultaneous illumination to a plurality of particles. Therefore, in the conventional flow cytometer, the laser diode 1 is mounted so that the major diameter of the elliptic section of the laser beam LB is arranged so as to be parallel to the flowing direction of the sample liquid T in the flow cell 6.

However, the above-mentioned arrangement causes a significant demerit. FIG. 3 shows a relationship between such as an arrangement and an intensity of the detected forward scattered light signal. In FIG. 3, the laser beam LB has such a large radiation angle $\theta$ in the direction parallel to the flowing direction of the sample liquid T, that the laser beam LB is partially kicked at upper and lower edges 3a and 3b of the collimator lens 3 to generate stray beams SB1 and SB2. Therefore, the stray beams SB1 and SB2 are focused on focal points BS1 and BS2 above and below a beam spot BS0 focused by a main beam MB in the flow of the sample liquid T. As a result, signals S1 and S2 (hereinafter referred to as "stray beam signal") attributed to the stray beams SB1 and SB2 are detected in addition to a particle signal S0 due to the main beam MB.

The stray signals S1 and S2 are mistakenly detected as small particle signals, which have a bad influence on the counting and classifying result of the particles to be analyzed. This demerit also applies to each detection of a sideward scattered light signal, backward scattered light signal and fluorescent signal, besides the detection of the forward scattered light signal.

To overcome the above-mentioned problems, the following attempt in a signal processing system is taken. In the system, a threshold value Vth is set to a value so as to detect the particle signal S0 but the stray beam signals S1 and S2 as shown in FIG. 4. That is, the "threshold value Vth" here is used for selecting the particle signal S0 in a series of signals S1, S0, S2. The signal intensity (peak level) VP and the light emitting period (pulse width) PW are calculated based on a part of the signal which exceeds the threshold value Vth.

In case where there is a great difference in pulse size between the particle signal S0 and the stray beam signals S1 and S2 (each of the stray beam signals S1 and S2 has a pulse smaller than that of the particle signal S0). For example, in case a relatively large-sized particle such as a blood cell is a particle to be detected, higher setting of this threshold value Vth enables to detect only the particle signal S0 and not to detect the stray beam signals S1 and S2. Accordingly, the laser diode 1 is provided in the conventional general flow cytometer such that the major diameter of the elliptic section of the emitted laser beam LB is arranged so as to be parallel to the flowing direction of the sample liquid T in the flow cell 6, whereby the above-mentioned merits (1. increasing the amount of light at the beam spot; and 2. decreasing the diameter of the beam spot) can be enjoyed.

However, when the sample includes particles of various size (for example, a diameter of about 0.5 to 100 microns), the threshold value Vth is required to be set lower corresponding to the minimum particle signal S0. Therefore, the stray light signals S1 and S2 exceeds the threshold value Vth and are detected by mistake as small-sized particles. This causes a miscount of the particles or gives an adverse affect to the pulse width information of the particle signals. For example, urine contains bacteria, red blood cells, white blood cells, epithelial cells, casts or the like, each of which has a various size. Particularly, the bacteria is greatly smaller than the other particles in most cases. In case of detecting these particles, the threshold value Vth for detecting the particle signal S0 should be set lower in order to detect the bacteria. Therefore, the stray beam signals S1 and S2 generated with the particle signal S0 of the white blood cell brings an analysis result as if the bacteria is also detected, although only the white blood cell should originally be detected. Further, the pulse width PW of the particle signal S0 of the white blood cell becomes greater than the original width, whereby the white blood cell may be analyzed as another type.

As described above, the adverse affect of the stray beam signals S1 and S2 is more remarkable in a flow cytometer that is required to detect not only large-sized particles but also small-sized particles.

If an attempt in the optical system is made for overcoming the above-mentioned problem, a laser diode having a narrower radiation angle is considered to be selected as the laser diode 1 in the optical system shown in FIG. 3 so that the laser beam LB does not impinge on the upper and lower edges 3a and 3b of the collimator lens 3. However, the laser diode generally has a feature that the radiation angle is determined by the wavelength of the laser beam. Further, the wavelength of the laser beam is necessarily determined by the character or kind of a particle to be analyzed. Accordingly, the laser diode having a narrow radiation angle of the laser beam cannot freely be selected.

For example, supposing that a fluorescent staining is performed in advance to blood cells in blood or material components in urine, obtaining fluorescent information from a fluorescent portion of each particle requires a laser beam having a relatively short wavelength, e.g., 700 nm or less. However, the laser diode generally has a characteristic that, the shorter the wavelength of the emitted laser beam becomes, the wider the radiation angle becomes. When a laser diode that emits a laser beam of relatively short wavelength is obliged to be used, the radiation angle of the laser beam inevitably increases. Therefore, the laser beam is partially kicked at the upper and lower edges 3a and 3b of the collimator lens 3, thereby causing the problem of generating the stray beam signals SB1 and SB2.

Bringing the laser diode 1 close to the collimator lens 3 or using a collimator lens having a large diameter is considered as another attempt for preventing the laser beam from impinging on the upper and lower edges 3a and 3b of the collimator lens 3.

In such a case, the collimator lens 3 is required to have a greater NA in order to bring the laser diode 1 close to the collimator lens 3. However, when a spherical lens is used as the collimator lens 3, there is a physical limit upon increasing NA with the lens diameter kept constant.

To use a collimator lens having a greater diameter, the lens is required to increase its diameter with the same curvature (i.e., a collimator lens having a greater NA is required to be used). However, there is also a physical limit upon increasing a lens diameter without changing the curvature.

On the other hand, it is not preferable to use an aspherical lens as the collimator lens 3. This is because the aspherical lens is unsuited to the collimator lens 3 from the viewpoint of the level of the current lens manufacturing technique.

There is another attempt in which a slit is provided between the laser diode 1 and the collimator lens 3 for limiting the radiation angle of the laser beam so as not to prevent the laser beam from impinging on the upper and lower edges 3a and 3b of the collimator lens 3. However, this attempt causes a great loss of the amount of beam. Further, the laser beam contacting edges of the slit is scattered, so that stray beams are likely to occur.

Accordingly, the above-mentioned problems cannot be perfectly solved by the aforementioned attempts.

SUMMARY OF THE INVENTION

The present invention is accomplished in view of the above subjects, and aims to provide a flow cytometer that prevents the generation of the stray beam signals by devising the angle at which the laser diode is arranged, whereby only the particle signal due to the main beam can effectively be detected.

The present invention provides a flow cytometer including a flow cell for flowing a sample liquid in a flowing direction to form a sample flow, the sample liquid containing particles to be analyzed, a laser diode radiating a laser beam having an elliptic cross section, a beam collimating section for collimating the laser beam radiated from the laser diode, a beam spot forming section for focusing the collimated beam at the sample flow in the flow cell to form a beam spot, and a light receiving section for receiving light generated from the particles at the beam spot to detect optical information of the particles, wherein the laser diode is arranged such that a minor diameter of the elliptic section of the laser beam is parallel to the sample flow.

BRIEF DESCRIPTION OF THE DRAWINGS

FIGS. 7(a) and (b) are views each showing an optical structure of a detecting section in the flow cytometer according to an embodiment of the present invention;

FIGS. 12(a) and (b) are explanatory views each showing an optical system of a modified example in the invention.

DESCRIPTION OF THE PREFERRED EMBODIMENT

Figure 1:
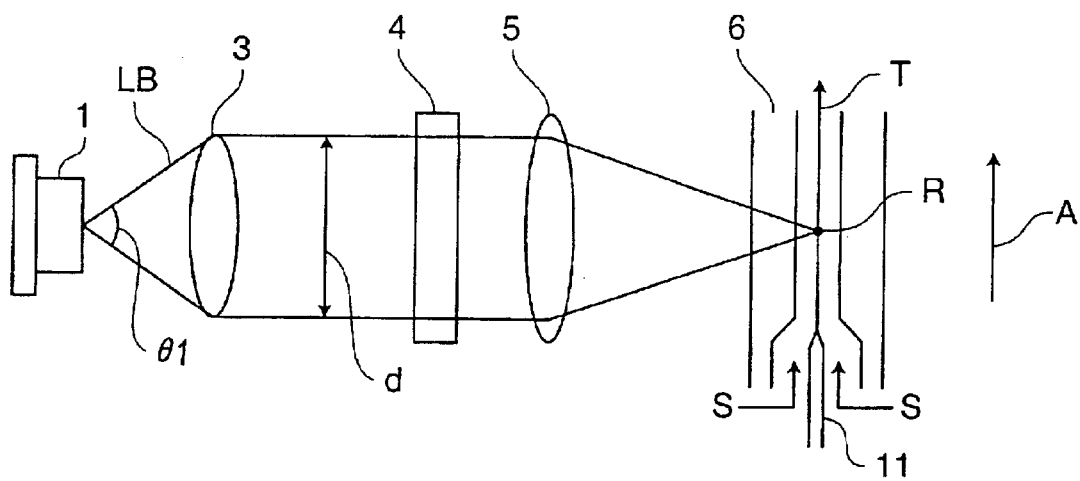
FIG. 1 is a schematic view showing one example of an optical system of a conventional flow cytometer.
Figure 2:
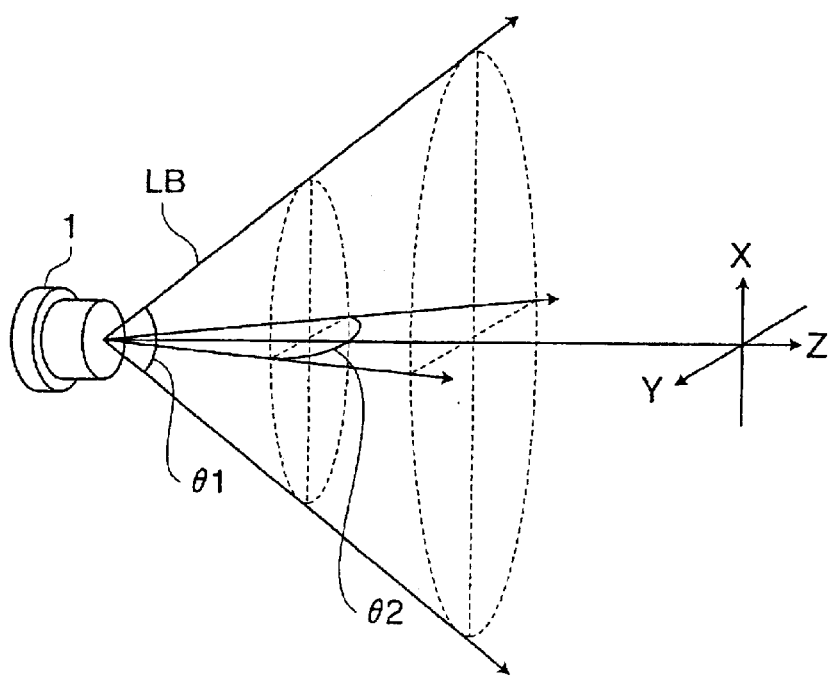
FIG. 2 is a view showing a state of laser light emitted from a laser diode.

A flow cytometer according to the present invention includes a flow cell for flowing a sample liquid in a flowing direction to form a sample flow, the sample liquid containing particles to be analyzed, a laser diode radiating a laser beam having an elliptic cross section, a beam collimating section for collimating the laser beam radiated from the laser diode, a beam spot forming section for focusing the collimated beam at the sample flow in the flow cell to form a beam spot, and a light receiving section for receiving light generated from the particles at the beam spot to detect optical information of the particles, wherein the laser diode is arranged such that a minor diameter of the elliptic section of the laser beam is parallel to the sample flow.

The particles to be analyzed in the present invention mainly include various blood cells contained in blood such as red blood cells, white blood cells and blood plate lets or material components contained in urine such as bacteria, red blood cells, white blood cells, epithelial cell and casts, but are not limited to these. The sample liquid is prepared by suitably performing a process such as dilution or staining, in case where the subject to be measured is, for example, a specimen such as blood or urine.

The flow cell used in the present invention is preferably transparent and has a smooth surface in order to obtain exact optical information from a particle passing therethrough. A material such as a glass is used for the flow cell. The laser diode used in the present invention is selected among those emitting a laser beam having a wavelength suitable for the character or kind of the particle to be analyzed.

The beam light collimating section is used to collimate the laser beam emitted from the laser diode. A collimator lens is preferably used for the section.

The beam spot forming section focuses the collimated beam at the sample flow in the flow cell to form a beam spot. A condenser lens is preferably used for the section.

The minor diameter of the elliptic beam spot formed at the sample flow preferably matches to the size of the particle to be analyzed. It is, for example, about 10 microns in the flowing direction of the sample liquid in the case of using a urine specimen as the subject to be measured.

The light receiving section used in the present invention detects, as optical information, a change in light intensity of scattered light or fluorescence generated when the particle to be analyzed in the sample liquid passes across the beam spot. The preferable one photoelectrically converts such optical information into a pulsed electrical signal. Preferable examples of the light receiving section include a photodiode, phototransistor, photomultiplier tube or the like.

The wavelength of the laser light emitted from the laser diode may be 700 nm or less in the present invention. The sample liquid may be prepared using a urine specimen. The particles to be analyzed may be bacteria.

The flow cytometer of the present invention may further comprise a cylindrical lens system, arranged between the light collimating section and the beam spot forming section, for adjusting a beam diameter and a focusing position of the laser beam with respect to a direction perpendicular to the sample flow, a beam stopper for shielding the laser beam passing through the flow cell from the light receiving section, and a condenser lens for converging the light generated from the particles to the light receiving section.

In the present invention, the cylindrical lens system may include a first cylindrical lens for converging the laser beam with respect to the direction perpendicular to the sample flow and a second cylindrical lens for diffusing the laser beam with respect to the direction perpendicular to the sample flow.

The cylindrical lens system may adjust the laser beam such that the beam spot at the sample flow forms an ellipse having a major diameter perpendicular to the sample flow and the laser beam passing through the flow cell forms an elliptic beam spot on the beam stopper, the elliptic beam spot on the beam stopper having a minor diameter perpendicular to the sample flow.

The sample flow may be sheathed with a sheath flow in the flow cell, the beam spot at the sample flow having a major diameter substantially equal to a width of the sample and sheath flows and the minor diameter of the elliptic beam spot on the beam stopper is minimized.

The beam stopper may include of an elongated shielding member extending along the sample flow and arranged at the focusing position of the laser beam adjusted by the cylindrical lens system.

The first cylindrical lens may include a convex cylindrical lens and the second cylindrical lens may include a concave cylindrical lens.

Figure 3:
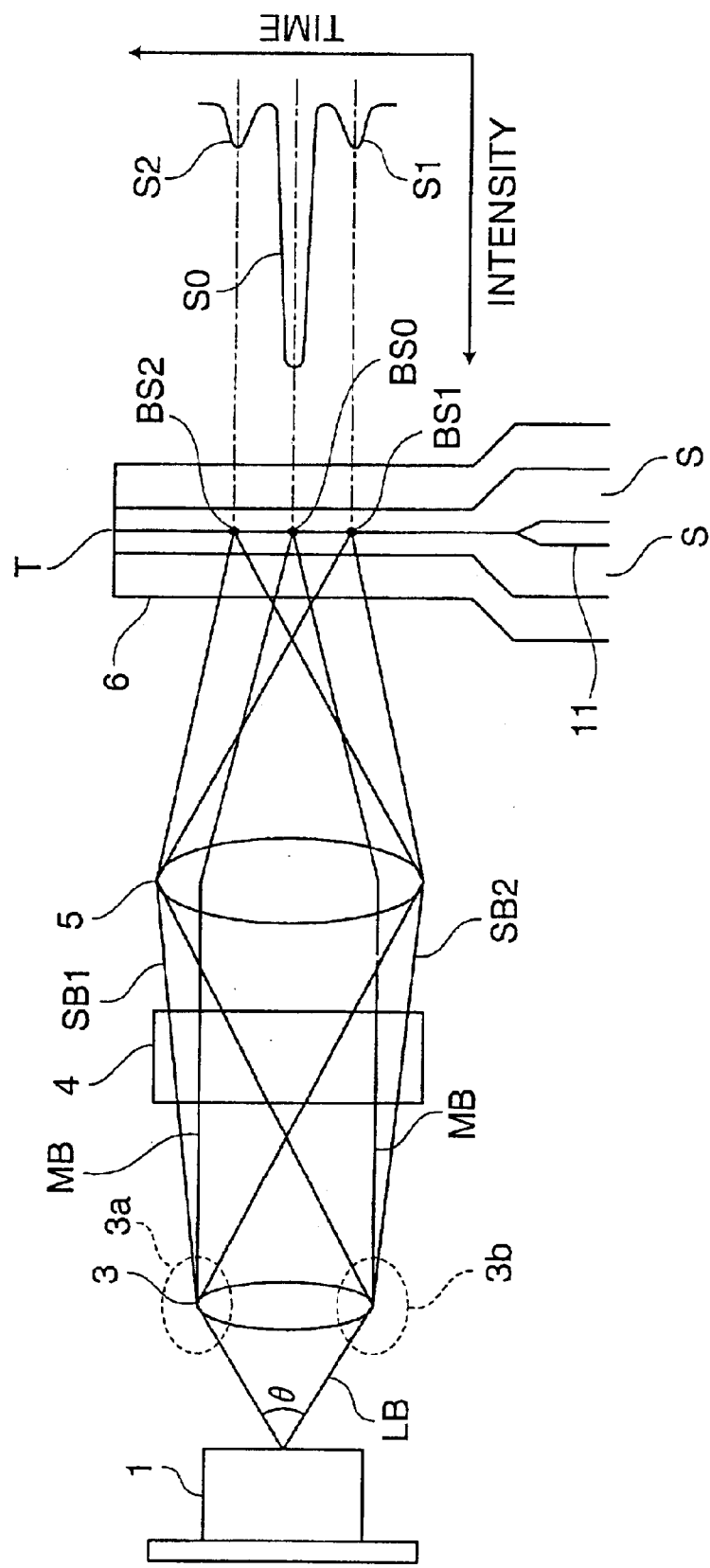
FIG. 3 is a view showing a state in which a forward scattered light signal is detected in the optical system of the flow cytometer.
Figure 4:
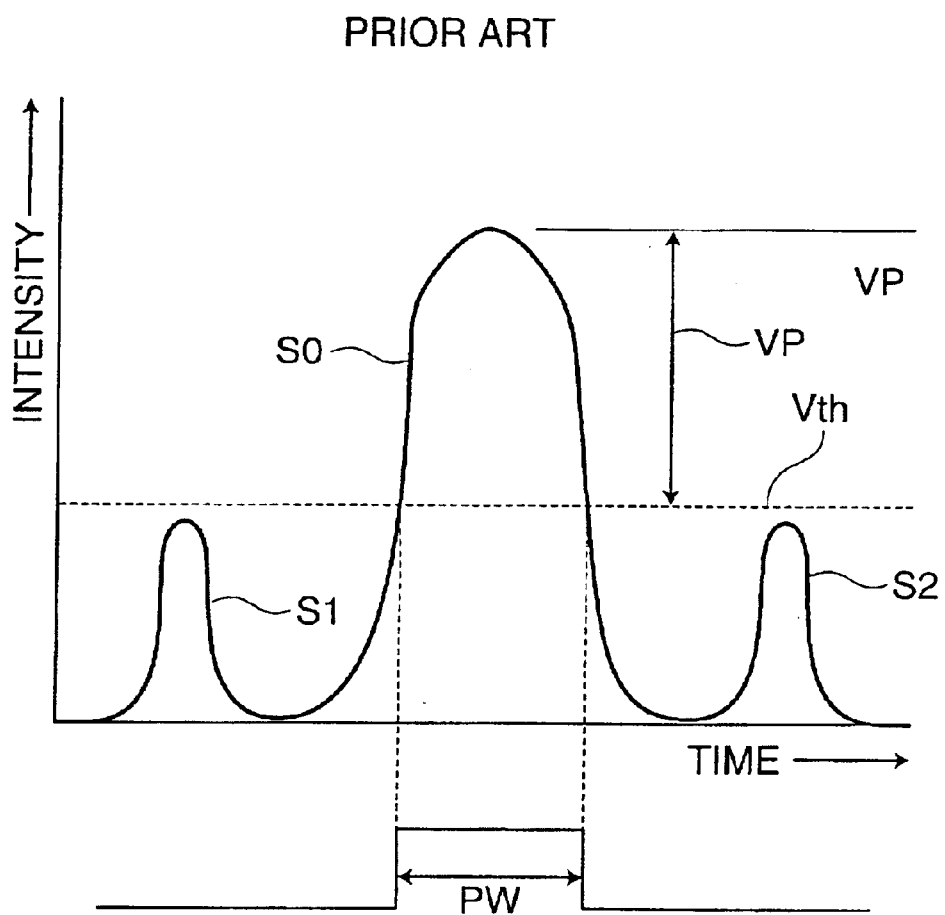
FIG. 4 is a view showing a relationship among a threshold value, peak level and pulse width in a pulsed electrical signal that detects a particle.
Figure 5:
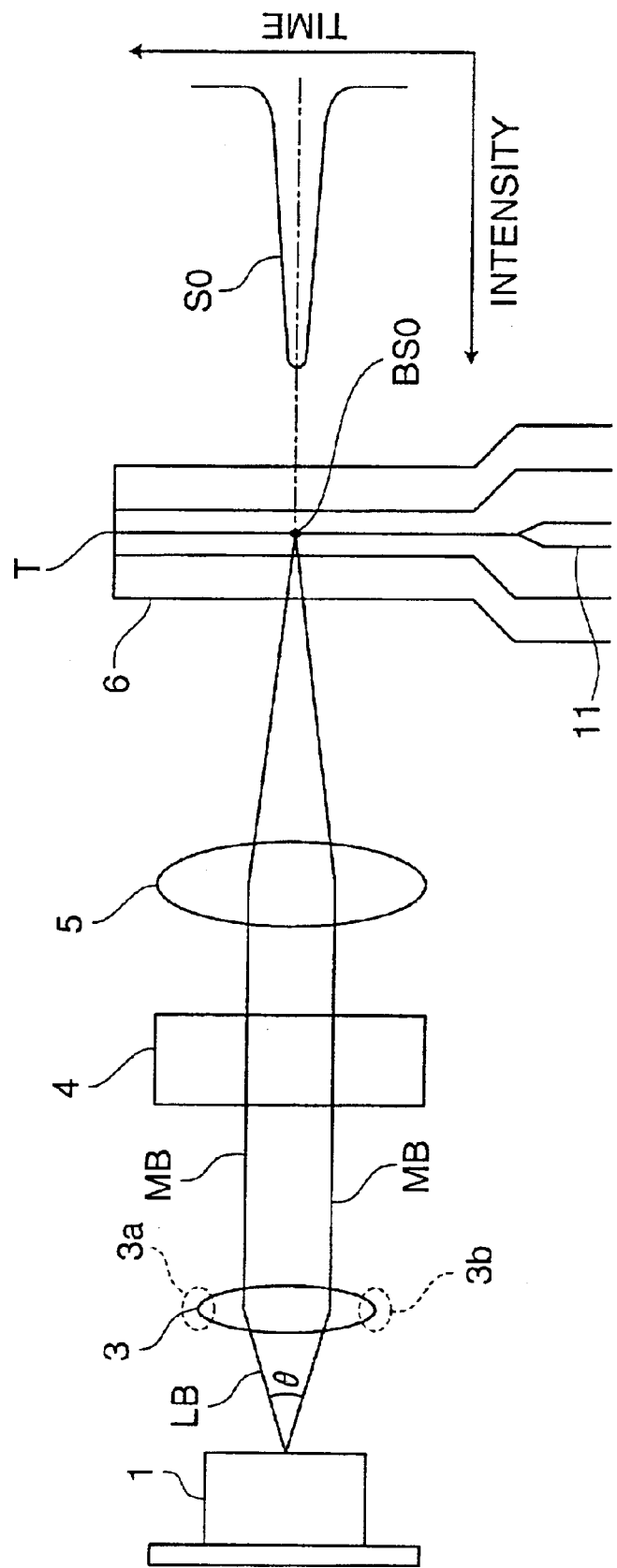
FIG. 5 is a view showing a state in which a forward scattered light signal is detected in the optical system of the flow cytometer.

FIG. 5 that corresponds to FIG. 3 shows the relationship between the optical system arrangement and the intensity of the forward scattered light signal according to the invention.

As shown in FIG. 5, the laser diode 1 is arranged in the present invention such that the minor diameter of the elliptic section of the emitted laser beam is parallel to the flow of the sample liquid in the flow cell. That is, the laser diode 1 is arranged so as to be rotated by an angle of 90 degrees compared to the conventional device.

The radiation angle θ of the laser beam LB emitted from the laser diode 1 is narrow in the longitudinal direction (flowing direction of the sample liquid) while wide in the lateral direction (direction across the sample liquid). This structure prevents that the laser beam LB is partially kicked at the upper and lower edges 3a and 3b of the collimator lens 3 to generate the stray beams. Accordingly, no stray beam focuses on any portions adjacent to the beam spot BS0 generated by the main beam MB in the sample flow in the flow cell 6, whereby any stray beam signals are not detected.

There is a possibility that the laser beam LB may be kicked at the right and left edges of the collimator lens 3 to generate stray beams. However, these stray beams do not focus on the sample liquid flow, but focus on the right and left portions of the beam spot BS0 (in the direction across the sample flow) out of the sample flow in the flow cell. Therefore, they are not detected as signals.

Such an arrangement of the laser diode 1 is particularly effective in case where a laser beam having a relatively short wavelength (i.e., a laser beam having a great radiation angle) is required to be used. Specifically, it is effective in the case of using a laser diode that emits a laser beam having a wavelength of 700 nm or less, for example, 635 nm. This is because when this type of laser diode is arranged such that the major diameter of the elliptic section of the emitted laser beam is conventionally parallel to the flowing direction of the sample liquid in the flow cell, the laser beam partially impinges on the upper and lower edges 3a and 3b of the collimator lens 3 to thereby generate stray beams.

Figure 6:
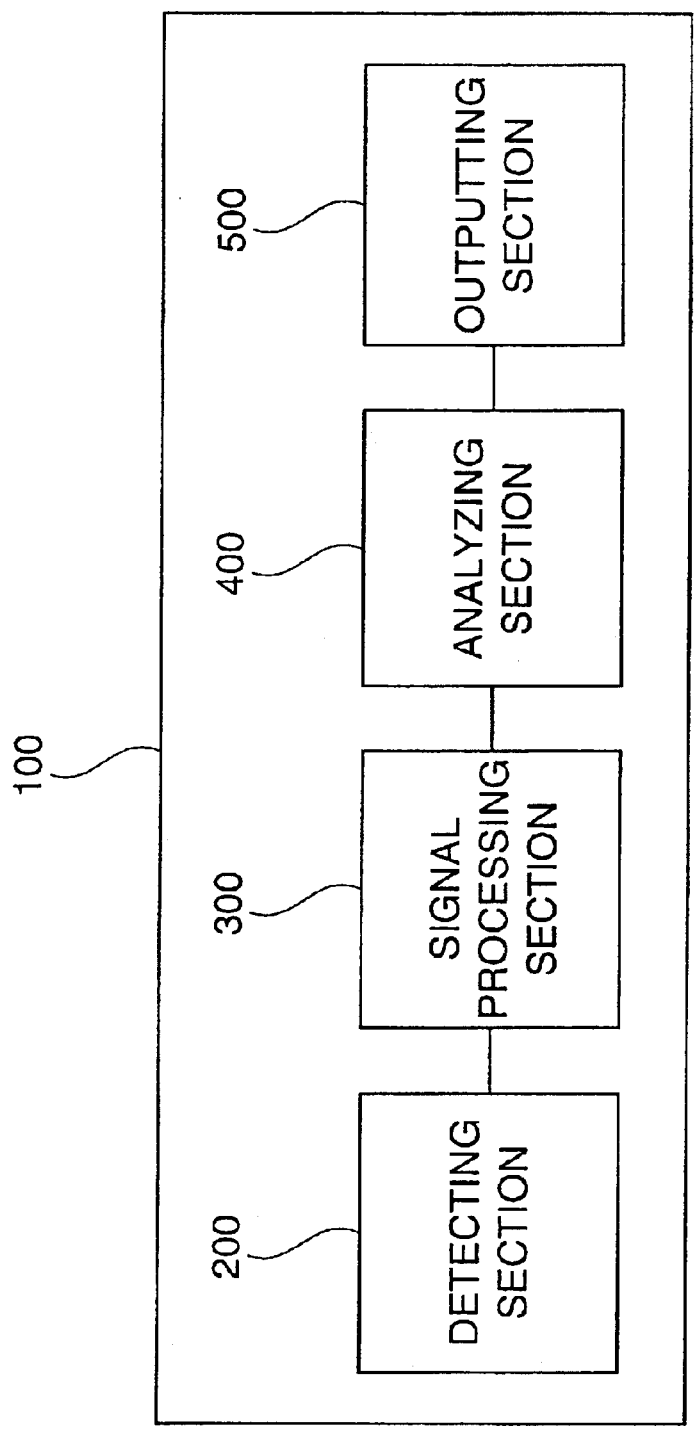
FIG. 6 is a block diagram schematically showing a structure of a flow cytometer according to the present invention.

The optical system of the present invention as explained above can be applicable to a known flow cytometer. FIG. 6 schematically shows a block diagram of the flow cytometer according to the invention. A detecting section 200 that is composed of the optical system explained above detects a pulsed electrical signal from an individual particle to be analyzed. This electrical signal is sent to a signal processing section 300 that comprises a circuit for processing the waveform of the pulsed signal obtained from the detecting section 200 to calculate various parameters. The calculated parameters include, for example, a peak level, a pulse width or the like. These parameters are calculated by a known peak hold circuit, a counter circuit, and the like.

The calculated various parameters is sent as particle data to an analyzing section 400 that analyzes the corresponding particle by statistically analyzing the particle data. The analyzing section 400 can be made of a microcomputer. A histogram or a scattergram made by combining a plurality of parameters may be formed upon statistically analyzing the particle data.

The flow cytometer may further include an output section 500 for outputting a result analyzed by the analyzing section 400. A display such as a CRT or LCD or a printer such as a laser printer can be used for the outputting section 500.

Embodiment 1

Explained hereinbelow is embodiment 1 where the flow cytometer of the present invention is adapted to a flow cytometer for analyzing material components in urine.

A sample liquid containing particles to be analyzed is prepared by performing a dilution or staining process to a urine specimen. This apparatus also comprises the detecting section 200, signal processing section 300, analyzing section 400 and outputting section 500 as shown in FIG. 6.

FIGS. 7(a) and 7(b) respectively show a construction of an optical system at the detecting section 200 in the present embodiment. A red laser diode (HL 6312G manufactured by Hitachi Seisakusho) is used for the laser diode 1 that is a laser beam source. The red laser diode emits a laser beam having a wavelength of 635 nm and a elliptic cross section. Its radiation angle is 31 degrees in the major diameter direction of the elliptic section and 8 degrees in the minor diameter direction.

Figure 8:
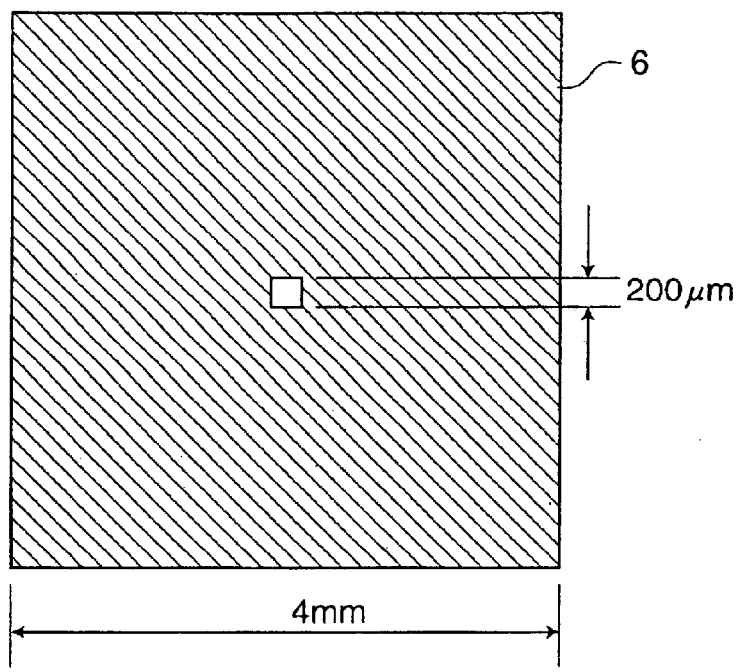
FIG. 8 is a sectional view of a flow cell used in the present invention.

The flow cell 6 is made of a glass and has a square cross section, one side of which is 4 mm as shown in FIG. 8. An inner flowing path having a square cross section, one side of which is 200 micrometers, is made along a longitudinal axis of the flow cell 6.

FIG. 7(a) is a side view of the flow cell 6 in which the optical system is seen from the direction perpendicular to the flowing direction of the sample liquid T. The sample liquid T containing the particles to be analyzed is supplied from the nozzle 11 to the flow cell 6 to form a sample flow. The laser beam LB emitted from the laser diode 1 is collimated by the collimator lens 3 that is the beam collimating section, and then, passes through the concave cylindrical lens 4 without causing a refraction to focus on a focal point SP1 in the sample flow in the flow cell 6.

FIG. 7(b) is a top view of the flow cell 6 in which the optical system is seen from the direction parallel to the flowing direction of the sample liquid T. The laser beam LB emitted from the laser diode 1 is collimated by the collimator lens 3. The collimated laser beam focuses on a second focal point SP2 behind the sample flow in the flow cell 6 by the condenser lens 5 after the beam diameter of the collimated laser beam is enlarged by the light diffusion function of the concave cylindrical lens 4.

Figure 9:
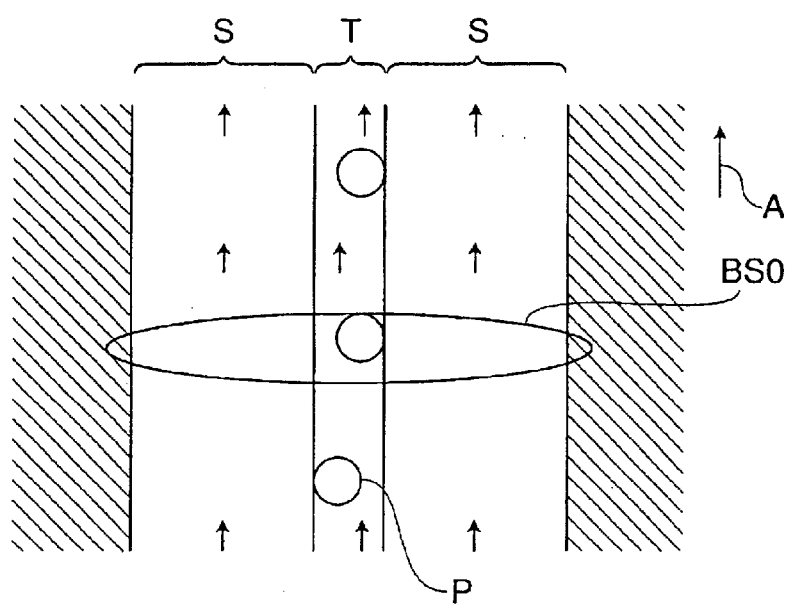
FIG. 9 is a typical view showing a state in which a beam spot is formed at the flow cell in the invention.

The above-mentioned optical arrangement can form an elliptic beam spot at the focal point SP 1 of the flow cell 6. FIG. 9 is a typical view showing a state where the beam spot BS0 is formed on the flow cell 6 when the flow cell is observed from an incident direction of the laser beam LB. At the beam spot BS0, the minor diameter of the elliptic section matches to the flowing direction of the sample liquid T (direction shown by an arrow A) by the condenser lens 5. This effectively prevents a plurality of particles P from simultaneously passing across the beam spot BS0. The concave cylindrical lens 4 allows the major diameter of the elliptic section to match in direction to the direction perpendicular to the flowing direction A of the sample liquid and to substantially match in length to a flow width of the sample liquid T and the sheath liquid S, whereby the particle P which shifts in the direction perpendicular to the flowing direction can fully be detected. In the present embodiment, the minor diameter of the beam spot BS0 is set to be 10 microns by the condenser lens 5 and its major diameter is set to be 220 microns by the concave cylindrical lens 4.

The irradiation of the laser beam LB produces forward scattered light FS from the particle P that flows through the flow cell 6. The forward scattered light FS is converged by a focusing lens 7 on a photodiode 8 to be photoelectrically converted into a pulsed electrical signal. The laser beam LB (direct beam) from the focusing lens 7 is cut by a beam stopper 9 while external stray light is cut by a pinhole plate 10 having a pinhole, so that S/N ratio of the electrical signal detected by the photodiode 8 is enhanced.

The signal detected at the detecting section 200 as described above is transmitted to the signal processing section 300 where a signal waveform of the signal is processed for calculating parameters such as a peak level, pulse width or the like.

Various parameters calculated as particle data by the signal processing section 300 is transmitted to the analyzing section 400 to be statistically analyzed. At the analyzing section 400, a scattergram is formed by combining two parameters of the forward scattered light signal, i.e., the peak level and the pulse width, and the particles to be analyzed are counted and classified.

An analyzed result is outputted by the outputting section 500. In the present embodiment, the data relating to various measuring items are printed out by a printer and the scattergram formed at the analyzing section 400 is displayed by a LCD.

Although the present embodiment refers only to the detection of the forward scattered light, a structure capable of detecting the fluorescence is naturally possible. Such a structure can be accomplished by the addition of a light receiving section for detecting a fluorescence signal and other necessary optical systems. Known devices can be utilized for the light receiving section and other necessary optical systems. For example, a photomultiplier tube is preferably used for the light receiving section.

Explained hereinbelow is an experiment for proving the effect of the flow cytometer according to the present invention. A flow cytometer having a conventional structure is used as a comparative example. The flow cytometer of the invention and the comparative example are those for analyzing material components in urine. Therefore, the threshold value Vth in each flow cytometer for detecting particles is set low enough to detect bacteria. The difference between the flow cytometer of the invention and the comparative example exists in the arranging direction of the laser diode in the detecting section. In the comparative example, the laser diode 1 is arranged such that the major diameter of the elliptic section of the emitted laser beam LB is parallel to the flowing direction of the sample liquid T in the flow cell 6. On the other hand, in the flow cytometer of the present invention, the laser diode 1 is arranged such that the minor diameter of the elliptic section of the emitted laser beam LB is parallel to the flowing direction of the sample liquid T in the flow cell 6.

Latex particles each having a diameter of 7 microns are used as particles to be analyzed. The latex particles are assumed as white blood cells contained in urine. The forward scattered light signal is detected by using these particles for making an observation and comparison of the signal waveform and scattergram.

Figure 10A:
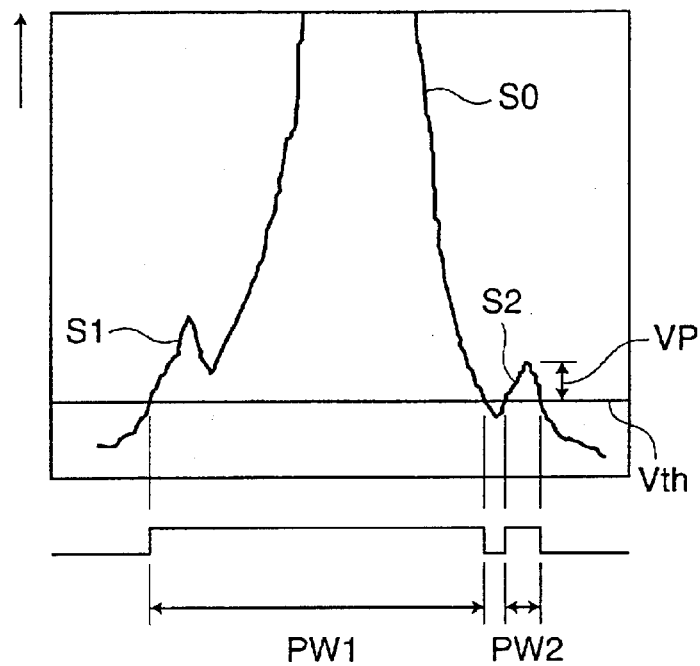
FIGS. 10(a) and (b) are views each showing a signal waveform when a latex particle is detected according to a conventional example and present invention respectively.

FIG. 10(a) shows a signal waveform in the forward scattered light signal of the 7 micron-diameter latex particle detected by the comparative example. Observing this waveform, it is found that signals (stray beam signals) S1 and S2 attributed to stray beams appear at the right and left of the signal (particle signal) S0 of the latex particle itself. The stray beam signal S1 appearing at the left of the particle signal S0 results in the calculation of a pulse width PW1 that is different from a pulse width of the latex particle signal S0. If the same state occurs in the case of measuring an actual urine specimen, particles that should originally be detected as white blood cells may mistakenly be detected as particles of another type. Further, the stray beam signal S2 appearing at the right of the particle signal S0 is detected as a small-sized particle independent of the 7 micron-diameter latex particle and a peak level Vp or pulse width PW2 corresponding to the small-sized particle is measured. This produces an error in a counting result of the particles. If the same state occurs in the case of measuring an actual urine specimen, an analyzed result may be obtained as if the specimen also contained small-sized particles, e.g., bacteria even through it contains only white blood cells.

Figure 10B:
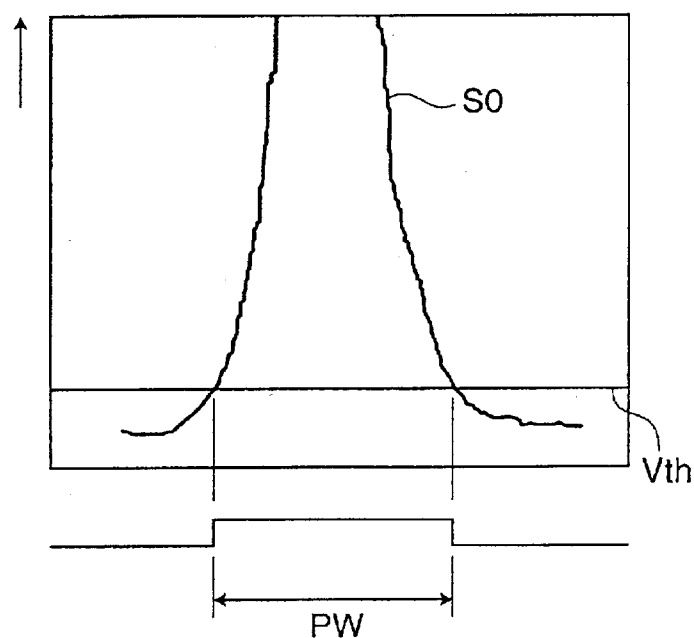

FIG. 10(b) shows a signal waveform in the forward scattered light of the 7 micron-diameter latex particle detected by the flow cytometer of the present invention. In this waveform, any stray beam signals do not occur and only a single pulse signal S0 representative of the 7 micron-diameter latex particle occurs. This shows that the adverse affect to the analyzed result due to the stray beam signal is eliminated and an accurate pulse width PW can be measured.

Figure 11A:
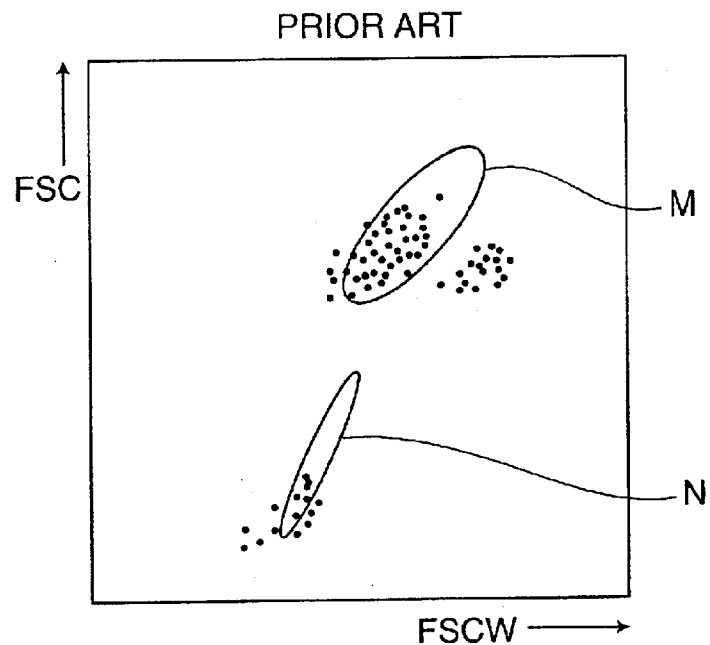
FIGS. 11(a) and (b) are views each showing a scattergram upon detecting a latex particle according to a conventional example and present invention respectively.

FIGS. 11(a) and (b) are scattergrams based on the forward scattered light signal of the 7 micron-diameter latex particle, wherein a peak level, i.e., a forward scattered light signal intensity (FSC) is used as a parameter for an ordinate while a pulse width of the forward scattered light signal (FSCW) is used as a parameter for an obscissa. In each scattergram, white blood cells and bacteria are supposed to be distributed in elliptical areas M and N, respectively. Such distribution areas M and N can be determined based upon the result by measuring in advance several kinds of known particles.

The scattergram of in FIG. 11(a) shows a result obtained by the comparative example. The particle to be analyzed has a diameter of 7 microns (corresponding to a white blood cell), so that particles should originally be distributed only in the white blood cell area M. However, it is found that the particles are distributed in the area other than the white blood cell area M due to the influence of the stray beam signals. That is, the particles detected as large-sized particles from the value of the pulse width influenced by the stray beam signals are distributed at the right side of the white blood cell area M, while the particles detected mistakenly as small-sized particles are distributed in the vicinity of a bacteria area N.

Figure 11B:
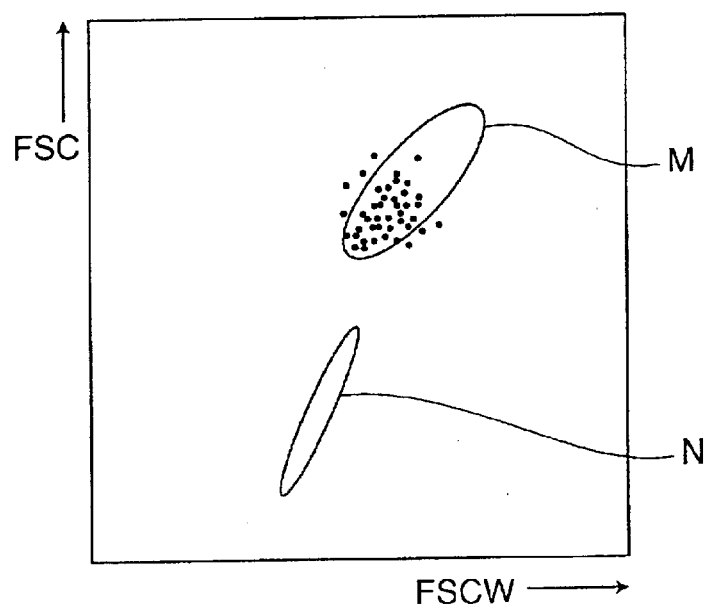

The scattergram of FIG. 11(b) shows a result obtained by the flow cytometer of the present invention. The result is unaffected by any stray beam signals, so that the distribution of particles is concentrated in the white blood cell area M.

The flow cytometer of the present invention enables to detect only the particle signal generated by the main beam without producing the signal due to stray beam conventionally generated at the edges of the collimator lens. Therefore, more accurate analyzed results can be obtained.

According to the invention, the adverse affect due to the stray beam signals can be avoided in case where the particles to be analyzed contain small-sized particles such as bacteria. That is, the remarkable effects of the present invention are achieved by the attempt at the optical system.

Embodiment 2

FIGS. 12(a) and (b) illustrate another embodiment in which the detecting section 200 is modified as follows. That is, the cylindrical concave lens 4 shown in FIGS. 7(a) and (b) is replaced with a cylindrical lens system comprising a convex cylindrical lens 4a and a concave cylindrical lens 4b. The other constructional elements are the same as those shown in FIGS. 7(a) and (b).

This modified embodiment has a purpose that the second focal point SP2 shown, in FIG. 7(b) is displaced to be present on the beam stopper 9 as shown in FIG. 12(b) for decreasing a width W of the beam stopper 9, whereby a larger amount of the forward scattered light from the particle can effectively be detected by the photodiode 8.

As shown in FIG. 12(a), the sample liquid containing the particles to be analyzed is ejected from the nozzle 11 to the flow path of the flow cell 6 to form a sample flow of the sample liquid T surrounded by the sheath flow, i.e., the sheath liquid S as shown in FIG. 9. In FIG. 12(a), the radiant laser beam LB emitted from the laser diode 1 is collimated by the collimator lens 3, and then, passes through the convex cylindrical lens 4a and the concave cylindrical lens 4b without refraction. Thereafter, the laser beam LB focuses on the first focal point SP1 at the sample flow in the flow cell 6, and then, reaches the beam stopper 9 having a length L.

On the other hand, in FIG. 12(b), the laser beam LB is emitted from the laser diode 1 and collimated by the lens 3. The collimated beam is reduced and enlarged in beam diameter by refraction functions of the convex cylindrical lens 4a and the concave cylindrical lens 4b, and then, converged at the second focal point SP2 on the beam stopper 9 by the condenser lens 5. In other words, the beam spot diameter of the laser beam LB formed on the beam stopper 9 is minimized in the direction perpendicular to the flowing direction of the sample liquid T.

The position of the second focal point SP2 and the major diameter of the beam spot BS0 (see FIG. 9) are independently determined according to focal distances of the convex cylindrical lens 4 and the concave cylindrical lens 5 and their setting positions.

That is, as shown in FIG. 9, the laser beam LB forms the elliptic beam spot BS0 having a major diameter of 220 microns and a minor diameter of 10 microns in the sample liquid T in the flow cell 2, and then, passes through the flow cell 2 to be cut by the beam stopper 9. However, in this modified embodiment, the cut laser beam LB forms on the stopper 9 such an elongated elliptic beam spot having a major diameter in the flowing direction of the sample liquid T that the width W of the beam stopper 9 can be extremely reduced.

Accordingly, the laser beam LB is effectively shielded by the elongated beam stopper 9, whereby the photodiode 8 can receive even low-angle light among the forward scattered light FS.

What is claimed is:

1. A flow cytometer, comprising:
    a flow cell for flowing, therein, a sample liquid in a flowing direction to form a sample flow, the sample liquid containing particles to be analyzed;
    a laser diode radiating a laser beam having an elliptic cross section;
    a beam collimating section for collimating the laser beam radiated from the laser diode;
    a beam diffusing section for diffusing the collimated beam in a direction perpendicular to the flowing direction;
    a beam spot forming section for focusing the diffused beam at the sample flow in the flow cell to form a beam spot, the beam spot being an ellipse having a minor diameter in the flowing direction and a major diameter perpendicular to the flowing direction; and
    a light receiving section for receiving light generated from the particles at the beam spot to detect optical information of the particles,
    wherein the laser diode is arranged such that a minor diameter of the elliptic cross section of the laser beam is parallel to the flowing direction.

2. A flow cytometer claimed in claim 1, wherein the laser beam radiated from the laser diode has a wavelength of 700 nm or less.

3. A flow cytometer claimed in claim 1, wherein the beam collimating section includes a collimator lens.

4. A flow cytometer claimed in claim 1, wherein the sample liquid is prepared by using a urine specimen.

5. A flow cytometer claimed in claim 1, wherein the particles include bacteria.

6. A flow cytometer claimed in claim 1, wherein the beam diffusing section includes a cylindrical lens.

7. A flow cytometer claimed in claim 6, wherein the cylindrical lens includes a concave cylindrical lens.

8. A flow cytometer claimed in claim 1, wherein the sample flow is sheathed with a sheath flow in the flow cell.

9. A flow cytometer claimed in claim 1, wherein the beam spot forming section includes a condenser lens.

10. A flow cytometer claimed in claim 1, further comprising:
    a condenser lens for converging the light generated from the particles to the light receiving section.

11. A flow cytometer claimed in claim 10, further comprising:
    a beam stopper, arranged between the flow cell and the condenser lens, for shielding a direct beam passing through the flow cell.

12. A flow cytometer, comprising:
    a light source for emitting a collimated light beam;
    a photoelectric detector;
    a flow cell for flowing, therein, a sample liquid in a flowing direction to form a sample flow, the sample liquid containing particles to be analyzed;
    a cylindrical lens system including a first cylindrical lens and a second cylindrical lens, the first cylindrical lens converging the collimated light beam in a direction perpendicular to the flowing direction and the second cylindrical lens diffusing the converged light beam in the direction perpendicular to the flowing direction;
    a first condenser lens for converging the diffused light beam at the sample flow in the flow cell to form a beam spot, the beam spot being an ellipse having a minor diameter in the flowing direction and a major diameter perpendicular to the flowing direction;
    a second condenser lens for converging light generated from the particles to the photoelectric detector; and
    a beam stopper, arranged between the flow cell and the second condenser lens, for shielding a direct beam passing through the flow cell.

13. A flow cytometer claimed in claim 12, wherein the cylindrical lens system adjusts the light beam such that the light beam forms a first beam spot on the sample flow and passes through the flow cell to form a second beam spot on the beam stopper, the first beam spot being shaped as an ellipse having a major diameter perpendicular to the sample flow, the second beam spot being shaped as an ellipse having a minor diameter perpendicular to the sample flow.

14. A flow cytometer claimed in claim 13, wherein the sample flow is sheathed with a sheath flow in the flow cell, the first beam spot having a major diameter substantially equal to a width of the sample and sheath flows and the minor diameter of the second beam spot is minimized.

15. A flow cytometer claimed in claim 12, wherein the beam stopper includes an elongated shielding member extending along the sample flow and arranged at a forming position of the light beam adjusted by the cylindrical lens system.

16. A flow cytometer claimed in claim 12, wherein the first cylindrical lens includes a convex cylindrical lens and the second cylindrical lens includes a concave cylindrical lens.

17. A flow cytometer claimed in claim 12, wherein the light source includes a laser diode radiating a laser beam having an elliptic cross section and a collimating lens for collimating the laser beam from the laser diode, the laser diode being arranged such that the elliptic cross section has a major diameter perpendicular to the sample flow.

* * * * *